United States Patent [19]

Kahn et al.

[11] 4,244,976

[45] Jan. 13, 1981

[54] INTERMEDIATE-MOISTURE FROZEN FOODS

[75] Inventors: Marvin L. Kahn; Kuttikandathil E. Eapen, both of Buffalo, N.Y.

[73] Assignee: Rich Products Corporation, Buffalo, N.Y.

[21] Appl. No.: 23,931

[22] Filed: Mar. 26, 1979

Related U.S. Application Data

[63] Continuation-in-part of Ser. No. 917,379, Jun. 20, 1978, abandoned, Ser. No. 871,995, Jan. 24, 1978, Pat. No. 4,154,863, and Ser. No. 763,613, Jan. 28, 1977, Pat. No. 4,146,652.

[51] Int. Cl.³ ............................................. A23L 1/32
[52] U.S. Cl. .............................. 426/330.1; 426/614; 426/327
[58] Field of Search ................ 426/330.1, 614, 321, 426/327

[56] References Cited

U.S. PATENT DOCUMENTS

| 1,724,078 | 8/1929 | Fousek | 426/330.1 |
| 2,395,587 | 2/1946 | Scott et al. | 426/330.1 |
| 3,409,446 | 11/1968 | Van Olphen | 426/614 |
| 4,001,449 | 1/1977 | Reardanz et al. | 426/614 |
| 4,046,922 | 9/1977 | Burkwall | 426/614 |

*Primary Examiner*—Jeanette M. Hunter
*Attorney, Agent, or Firm*—Kenyon & Kenyon

[57] ABSTRACT

A microbiologically stable intermediate moisture sugared egg yolk composition containing egg yolks, dextrose plus fructose, about water, and about stabilizer. This product is soft and non-crystalline at freezer temperature.

16 Claims, No Drawings

INTERMEDIATE-MOISTURE FROZEN FOODS

CROSS-REFERENCE

This application contains subject matter divided out of U.S. Pat. application Ser. No. 917,379, filed June 20, 1978 now abandoned, U.S. Pat. application Ser. No. 871,995, filed Jan. 24, 1978 now U.S. Pat. No. 4,154,863, and U.S. Pat. application Ser. No. 763,613, filed Jan. 28, 1977 now U.S. Pat. No. 4,146,652, and is also a continuation-in-part of said applications.

BACKGROUND OF THE INVENTION

A recent development in the food industry is the emphasis on intermediate-moisture foods which have the faculty of being stored and marketed in a substantially non-refrigerated condition. These foods were designed to avoid the need to be packaged in a hermetically sealed container and commercially sterilized or maintained in a frozen or refrigerated state throughout the period of distribution and storage by the consumer.

The intermediate-moisture foods are based on the principle of reducing the availability of water in the food for microbial growth. The availability for spore germination and microbial growth is closely related to its relative vapor pressure, commonly designated as water activity. It was found that the use of a wide variety of water-soluble solutes, or osmotic agents, has the effect of depressing the water activity of the foods to levels at which most bacteria will not grow.

The water activity of a food is defined as the partial pressure of water in the food divided by the saturation pressure of water at the temperature of the food. The water activity can be determined by placing a sample in a container which is then sealed, and after equilibrium is reached, determining the relative humidity above the sample. Most products of this type have between 10 to 40% moisture, and a water activity between 0.65 and 0.9.

An early application of the technique of controllling water activity was for animal foods. For example, U.S. Pat. No. 3,202,514, issued Aug. 14, 1965, discloses an animal food having 15 to 30% moisture and 15 to 35% water-soluble solids, principally sugar, with a proteinaceous meaty substance. Subsequently, other foods were formulated with an intermediate-moisture content, such as egg products (U.S. Pat. No. 3,640,731, issued Feb. 8, 1972), pancake batter (U.S. Pat. No. 3,753,734, issued Aug. 21, 1973) and whippable bases for confectionary use (U.S. Pat. No. 3,958,033, issued May 18, 1976). The water content and water activity of these foods are brought to as low a value as practical to insure their long-term stability withou refrigeration. The main difficulty with these foods is that their low-moisture content may detract from their palatability, texture and mouth-feel. This technique therefore has found its greatest commercial applicability in the pet-food market where palatability requirements are not as stringent.

It is of course desirable to be able to avoid refrigeration and freezing of food products to reduce the cost involved, and particularly for the consumer, to avoid the inconvenience of unpacking, handling, and then defrosting the typically rock-hard frozen foods. However, freezing is an extremely safe and suitable technique for long-term storage and provides the manufacturer with great leeway in incorporating any of a wide variety of ingredients in foods which would otherwise be short-lived.

Accordingly, a class of intermediate-moisture foods has been found in accordance with application Ser. No. 763,613, filed Jan. 28, 1977, and application Ser. No. 871,995, filed Jan. 24, 1978, which combines the convenience of the freezing method of storage sought by manufacturers with the ease of handling desired by consumers. Such foods are normally stored at freezer temperatures, but upon removal from the freezer can be ore readily handled because they retain a flexible consistency, are non-crystalline and spoonable within about 5 to about 15 minutes, and can be left at room temperature for an extended period of time as they possess the requisite microbiological stability.

The foods of the invention are generally characterized by a high sugar content, usually at least equal in weight to the amount of water present, in order to provide microbiological stability. The sugars employed have a low molecular weight, being primarily dextrose and fructrose, which comprise together at least about 50% and preferably at least about 75% of the total sugar content. Sucrose has a sweetness between that of fructose and dextrose. The fructose, which is sweeter than the dextrose, is preferred since it has a lesser tendency to crystallize and cause apparent hardness. For most foods, particularly where the food comprises an emulsion, it is preferred that the fats used, if any, include partially unsaturated fats which tend to provide superior flow properties and nutritional advantages, although less stable than saturated fats. The fat content is usually less than the water content in order to form a stable oil-in-water emulsion; the water content is preferably at least about 25% greater than the fat content.

The use of bacteriostatically effective amounts of sugar, however, imparts excessive sweetness to the ultimate food product. The problem of excessive sweetness has arisen previously in conjunction with the development of artificial sweeteners, and certain bitterness principles have been incorporated in such products to mask the undesirable taste. It was disclosed in U.S. Pat. No. 3,934,047, issued Jan. 20, 1976, that addition of aluminum potassium sulfate, naringen or a combination thereof to artificial sweeteners such as the saccharines or the cyclamates, or to higher caloric sweeteners such as sucrose, effectively reduced the perceived sweetness and bitter after taste of the artificial sweetener. It was postulated that the bitterness agent reduces the duration of sweetness, and presumably alters the manner in which sweetness is perceived.

In connection with neturalizing the bitter after taste of saccharine or saccharine salts, it was disclosed in German Patent No. 2,060,634, issued Dec. 9, 1970, that the addition of about from 0.2 to 2.0 by weight percent of one or more substances having a bitter taste results in masking of the lingering bitterness associated with saccharine. Quinine sulfate and magnesium sulfate are specifically recommended as additives for use in this regard.

Such bitterness principles as quinine, theobromine and caffeine have also been advanced for use as flavor factors in synthetic and natural chocolate compounds and chocolate-flavored beverages to impart a bitter taste to the resultant foodstuff. U.S. Pat. No. 2,835,592, issued May 20, 1958, and U.S. Pat. No. 3,102,815, issued Sept. 3, 1963, are illustrative of such disclosures.

Further flavor modifiers which impart a bitterness to the compounds in which they are incorporated are disclosed in U.S. Pat. No. 3,647,482, issued Mar. 7, 1972, to Yueh, and U.S. Pat. No. 4,006,261, issued Feb. 1, 1977, to Pickenhagen et al. Yueh's patent discloses the use of ribonucleotides, ribonucleosides and their deoxy analogues to reduce or eliminate the bitter after taste associated with saccharine or saccharine salts, or compositions containing these sweeteners. Pickenhagen et al. disclose the use of compositions of theobromine in combination with cyclic dipeptides to impart bitterness and astringency properties to various foodstuffs, especially cocoa products, animal foods, beverages, pharmaceutical preparations and tobacco products.

In U.S. Pat. No. 3,371,543, issued Feb. 13, 1973, the use of theobromine, caffeine or naringen to impart bitterness to nitrogen-based flavor intensifiers is disclosed.

It is an object of the present invention to provide a class of foods which are normally maintained at freezer temperature, but whic possess the requisite microbiological stability for storage at refrigerator or room temperature for an extended length of time without spoilage.

It is another object of the present invention to provide an improved bacteriostatic intermediate moisture food product which is ready for use at freezer temperature, the perceived sweetness of which has been reduced through the addition of a bitterness factor.

It is a further object of this invention to accomplish the above-specified reduction in sweetness perception through the use of certain quinine salts.

Other objects, and advantages, of this invention will be apparent from the ensuing specification and examples.

THE INVENTION

The present invention is directed to microbiologically stable intermediate-moisture foods and other products which are normally maintained at freezer temperature. The principles and techniques which have been developed for intermediate-moisture foods are applicable to the present invention, as modified in the manner explained herein below. Many of the foods of this invention are maintainable at freezer temperature in a condition ready for immediate use. After removal from the freezer the foods may be held at room temperature or at refrigerator temperature for a considerable period of time without spoilage because of the bacteriostatic effect of the sugar/water ratio.

The foods of this invention are generally characterized by a high sugar content, usually at least equal in weight to the amount of water present in order to provide microbiological stability. The sugars used have a low molecular weight, being primarily dextrose and fructose, which comprise together at least about 50% and preferably at least about 75% of the total sugar content. Sucrose has a sweetness between that of fructose and dextrose. The fructose, which is sweeter than the dextrose, is preferred since it has a lesser tendency to crystallize and cause apparent hardness. For most foods, particularly where the food comprises an emulsion, it is preferred that the fats used, if any, include partially unsaturated fats which tend to provide superior flow properties and nutritional advantages although less stable than saturated fats. The fat content is usually less than the water content in order to form a stable oil-in-water emulsion; the water content is preferably at least about 25% greater than the fat content.

The high levels of sugar requisite to effect bacteriostasis may render the ultimate food product excessively sweet, however, and thus less palatable to some consumers. In accordance with this invention, it has been found that the addition of a bitterness principle modifies the undesirable sweetness of the sugar. More specifically, addition of a quinine salt, such as quinine sulfate, quinine bisulfate or quinine hydrochloride, results in reduced perception of sweetness. In many cases, the perceived sweetness is reduced by more than half the value associated with the unmodified food product. Quinine salts are employed in this regard in amounts up to about 125 p.p.m. per food stuff. A preferred range of such additive amounts is from 2 to 75 p.p.m.

An important group of foods which has been particularly well-adapted in accordance with the present invention consists of the oil-in-water emulsions, including butter creams, whipped toppings, low-fat whipped creams, milk mates, non-dairy shakes, icings and coffee creamers.

Another class of goods, which forms a unique combination with the foregoing, is bakery products such as cakes, breads, cookies, pie shells, muffins, turnovers, pancakes, waffles and doughnuts. The pastries can be filled or topped with the creams and icings of this invention.

Many diverse foods can likewise be adapted pursuant to this invention, such as dressings, puddings, sauces, gravies, snack spreads, pancake syrups, ice creams, candies, and beverage (soup, tea, juice) concentrates, and meat, fish, fruit and vegetable products.

The foods of this invention are generally characterized by a water activity of about 0.75–0.90, up to about 0.93, a sugar to water ratio of about 1:1 and a sugar content which is at least 50% dextrose, fructose, or a combination thereof. In addition, many of the foods of this invention are adapted to remain spoonable or pourable at freezer temperature. Although most intermediate-moisture products will conventionally have a water activity below 0.85, some sacrifice in texture and taste may be required to meet this standard. Since the foods of this invention are maintained at freezer temperature until ready to be used, a water activity of 0.85–0.90, up to about 0.93, is adequate. Freezer temperatures of course are adequate to maintain the microbiological stability of foods and even moderate control of water activity is adequate to extend the useful life of these products after removal from the freezer. Freezer temperature, unless otherwise indicated, refers to temperatures of from about −5° F. to +10° F., which represents a common range for both home and store freezers.

The standard of being spoonable refers to the texture or flexibility of the product, as well as to the quality of being able to eat the food when it is at freezer temperature. The quality of being spoonable as used in this description is one which gives a satisfactory reading on a standard penetrometer and/or flow test, i.e., gave a penetrometer reading above about 3mm.

The products of this invention having a penetrometer reading of about 3 mm or below are substantially non-crystalline, however, and become spoonable within a very short period of time upon removal from freezer temperatures and introduction to room temperature (about 72° F.), generally within about 5 to about 15 minutes. Such non-crystalline-type products can be used immediately in mixing, blending and various other food preparation procedures, although generally not considered quite flexible or soft enough for immediate consumption.

Pourable products of this invention are more fluid and are tested by flow characteristics, generally about 30 ml per minute and higher during the first five minutes after removal from the freezers.

The products, of this invention present highly significant results when compared to the standard, rock-hard frozen products currently on the market. Details of the testing procedures are specified below.

The water activities of the foods of this invention are usually about 0.75 t 0.90. Generally, the water activity is at the higher end of this range, i.e., about 0.85–0.90, up to about 0.93. Although microbiological stability is inversely proportional to water activity, several desirable properties of food are adversely affected at very low water activity, e.g., mouth-feel and taste. Since the foods of this invention are normally held at freezer temperatures for long-term stability, it is practical to formulate foods which have water activities nearer the borderline of microbiological stability, which is about 0.90–0.93.

Several mathematical methods are available for calculating water activity, even of formulations containing different solutes and with non-solutes. Rough calculations based on the additive effect of the number of moles of each component multiplied by the activity of the component are useful for estimating water activity. Such calculations reduce the number of experimental measurements that might otherwise be needed and thus assist in reaching a suitable formulation more quickly. A combination of mathematical techniques with trial and error experiments followed by analytical measurements for determining water activity will lead to acceptable results.

There are commercially available devices for measuring the water activity of formulations. For example, a formulation may be placed in a container until equilibrium is reached and then the humidity in the container measured. The water activity is then determined through reference to standard tables. For example, electric hygrometers are devices commonly used to measure water activity. These devices contain sensors impregnated with salts such as lithium chloride or potassium chloride. Water is adsorbed on the sensor and causes a change in electrical resistance which is measured by a wheatstone bridge. Reference curves based on solutions of known humidity are used to relate the electrical readings to water activity.

Throughout this application all amounts are by weight unless stated otherwise. In the examples the amounts have been adjusted to a basis of 100. Percentages are based upon total formulation weight, unless a different basis is given.

Many of the foods of this invention are generally characterized as microbiologically stable food products comprising about from 15 to 45% water, sugar in a ratio to water of about 1:1 to 2:1, preferably about from 1.5-1:1, and minor but effective amounts of salt, emulsifier, stabilizer and flavoring, provided that the foregoing comprises at least one of fructose and unsaturated fat, that the amount of fat, if any, is less than the amount of water or equivalent phase, such as non-aqueous water-soluble liquid phase, the solutes content is adequate to provide the product with a water activity of about from 0.9–0.9, up to about 0.93, the amount of dextrose plus fructose is at least about 50% based upon the total sugar content, and wherein the foregoing ingredients are adapted to provide a product which is substantially non-crystalline at freezer temperatures.

Further, the foods of this invention may comprise up to about 125 p.p.m. of a quinine salt.

Certain other foods of the instant invention are characterized by the above general formulation exclusive of the restriction specifying that the ingredients comprise minor but effective amounts of salt, emulsifier and stabilizer, and the ratio to water of sugar. Other foods may comprise saturated fat, the total amount of fat comprising about from 2.5 to 30%.

A preferred class of foods is microbiologically stable oil-in-water emulsion cream-type products, such as butter creams, whipped creams, shakes, non-dairy creamers, etc., which comprise about from 25 to 45% water, sugar in a ratio to water of about from 1.5-1:1, about from 10 to 30% fat, and minor but effective amounts of protein, salt, emulsifier, stabilizer and flavoring, a water activity of about from 0.8 to 0.9, wherein the amount of fructose is about from 15 to 65% based on the sugar content and the amount of dextrose is at least about 50% based upon the remaining total sugar content, the fat content preferably contains at least about 10% unsaturated fat and the foregoing ingredients are adapted to provide a product which will flow at about 10° F. Such preparations may also comprise preferably about from 3 to 20 p.p.m. of a quinine salt. When the sugar component of the non-dairy creamer formulation is modified to contain only dextrose, a microbiologically stable food product is produced which remains semi-soft and substantially non-crystalline rather than spoonable at freezer temperature.

These oil-in-water emulsion products have excellent texture and eating properties and are readily whipped to a high volume with a light but firm structure. In addition to microbiological stability, these products have physical stability in that they retain a smooth foamed cellular structure without separation of a liquid portion. The products are further characterized by having an overrun of greater than about 150% and a density as low as about 0.3 or 0.4 for a butter cream and a whipped cream.

Another class of useful products is the flour-based foods. The batters for these products comprise conventional amounts and types of flour depending on the final product, about from 15 to 40% water, sugar in a ratio to water of about from 1.5-1:1, about from 2 to 10% or up to 25% fat, and minor but effective amounts of leavening agent which may be encapsulated, egg products, salt, emulsifier, stabilizer and flavoring, provided that the solutes content is adequate to provide the product with a water activity of about from 0.8 to 0.9, the fructose content of the sugar preferably is about 10 to 40%, the amount of dextrose plus fructose is at least about 50% or from 75 to 100% based upon the total sugar content, and the fat is preferably unsaturated. The batter should have at least one of fructose and unsaturated fat to assist in providing a spoonable and preferably a pourable product at about 10° F. The final product made from the batter has a higher penetrometer value that conventional products at 10° F. and is edible at that temperature. Such preparations may also comprise preferably about from 5 to 100 p.p.m. of a quinine salt.

A unique combination is prepared from a bakery product and a cream-type product, each made in accordance with this invention. Further, fruit (which may be infused with solutes) may be added to the bakery products and the cream-type products. The water activity of the bakery product and cream-type product when used in combination should be approximately the same, plus or minus 0.05 units, or up to 0.10 units deviation from each other. When the water activity values are comparable there is less of a tendency for water transfer as, for example, between a cake and its topping or filling.

Microbiologically stable soup concentrates and sauces have been made comprising about from 30 to 45% water, sugar in a ratio of water of about from 1.5-1:1, about from 5 to 30% fat, and minor but effective amounts of salt, stabilizer and flavoring, wherein the amount of dextrose plus fructose is at least about 50% based upon the total sugar content, the foregoing ingredients comprise at least one of fructose and unsaturated fat and the product is spoonable at about 10° F. Fish, meat and vegetables (which may be infused with solutes) are added to these to provide, for example, a chowder concentrate or newburg sauce. Such preparations may also comprise about from 5 to 100 p.p.m., preferably about from 30 to 70 p.p.m., of a quinine salt.

Microbiologically stable beverage concentates, for example, tea, orange juice, etc., are made in accordance with this invention. They generally comprise about from 35 to 45% water, sugar in a ratio to water of about 1.8-2:1, and minor but effective amounts of flavoring, provided that the amount of fructose plus dextrose is about from 75 to 100% based on the total sugar content and the amountof fructose is about from 10 to 30% based upon the total sugar content, wherein the foregoing ingredients are adapted to provide a product which will flow at about 10° F. Such preparations may also comprise preferably about from 5 to 50 p.p.m. of a quinine salt.

Microbiologically stable pudding products have been made comprising about from 25 to 45% water, sugar in a ratio to water of about from 2-1:1, about from 3 to 25% fat, preferably unsaturated, and minor but effective amounts of gelling agent, emulsifier, stabilizer and flavoring, provided that the amount of dextrose plus fructose is at least about 75% of the total sugar content, wherein the foregoing ingredients are adapted to provide a product which is spoonable at about 10° F. Such preparations may also comprise about from 5 to 75 p.p.m., preferably 10 to 20 p.p.m., of a quinine salt. Fruit, which may be infused with solutes, may be added to the pudding products of this invention. Suitable pudding products include bread, rice, and plum pudding.

Microbiologically stable meat products, such as hotdogs, hamburgers, sausages and various meat loaves, are also made in accordance with this invention. Standard recipes for such products, known to those skilled in the art, are modified through this invention to contain (1) enhanced amounts of sugar, preferably fructose, in place of conventional sugar now used in amounts up to several times greater than those presently employed or (2) an infused solution of sugar in a ratio to water of at least 1:1, and, in either case, (3) fat in an amount less than the amount of water or equivalent phase, wherein the fat is substantially unsaturated, i.e., 50% or more, or preferably 75% or more of the fat is unsaturated. Furthermore, a quinine salt may be added in an amount not exceeding 125 p.p.m., and preferably falling within the range of 7 to 75 p.p.m. These modifications are incorporated in the compositions of such meat products to provide increased microbiological stability and thus extend the shelf-life of such goods.

The apparatus for measuring the flow characteristics of the products of this invention was fabricated from stainless steel, and was essentially a stand 14"×12", with a movable platform of the same size to provide for vertical and angular adjustments. The platform was provided with a bulls-eye level and a protractor level; with the leading edge having a wire brace to retain the sample container.

The following method was used in obtaining the flow data. Graduated cylinders of 600 ml. capacity were filled with the samples and frozen for at least 24 hours at +5° F. The frozen samples were removed from the freezer, immediately placed on the platform in a horizontal (0°) position, and the effluent collected in other graduated cylinders, with the volume noted at timed intervals. Temperatures were monitored with a Honeywell recorder. Sample temperatures within the freezer varied from +4° F. to +7° F. over a four-week interval, but varied no more than 1° F. over an 8 hour period, while the temperature in the freezer varied from +5° F. to +15° F., each time the door opened. Room temperature varied about 2° F. for an average of 72° F., while the temperature of the samples in the original container rose anywhere from 1° F. to 14° F. during the 15 minutes after removal from the freezer.

The penetrometer test and equipment used are standard. The penetrometer is made by Labline Instrument Co. Inc., Chicago, Illinois. The device measures the penetration into the sample of the point of a hard rubber cone which weighs 12 grams and has a height of 1¼" and a diameter of 1¼" at its base. The inverted cone is supported by a freely-sliding bar which weighs 48 grams. For all measurements the sample was brought to a temperature of −7° F. in a freezer and then removed from the freezer and immediately tested.

The products of this invention exhibited freeze-thaw stability in storage. The products were kept in a supermarket-type freezer unit which cycled six times a day between application of cooling to freeze the product and application of heat to defrost the unit. Under these conditions the products remained acceptable and functional.

The liquid emulsions were examined by dipping a spatula in the emulsion, letting it drain and noting whether the residual film was smooth and uniform or whether particles were present, a condition denoting destabilization. These emulsions were also evaluated for their intended functional application.

The products passed the following test procedures:
(a) The non-dairy creamer concentrates were tested in coffee for whitening ability, signs of free oil on the surface or curdled appearance, and presence of oil globules or curdling indicating emulsion breakdown.
(b) The semi-solid products which are consumed as such, e.g., pudding and cocktail sauce, were tested for syneresis and appearance (texture).

The method of making a microbiologically stable food product of this invention generally comprises mixing together about from 15 to 45% water, sugar in a ratio to water of about from 2-1:1, about from 2.5 to 30% fat, and minor but effective amounts of salt, emulsifier, stabilizer and flavoring, provided that the amount of fat is less than the amount of water, the solutes content is adequate to provide the product with a water activity of about from 0.8 to 0.9, and the sugar comprises at least about 50% dextrose plus fructose; pasteurizing the mixture and cooling the resultant product. Up to about 125 p.p.m. of a quinine salt may also be employed in the mixing step.

A preferred method for preparing an emulsion product of this invention comprises blending all of the ingredients in the desired ratios. Usually most of the non-fat ingredients are first dispersed in the water. The ingredients are heated prior to or during blending. For example, the heating may begin during the mixing of the non-fat ingredients, and then the emulsifiers and fats added. The fat protein may also be preheated and then admixed. The ingredients are pasteurized by holding at an elevated temperature for several minutes, i.e., at 180° F. for five minutes.

The blended ingredients are then passed through a homogenizer of the typical dairy type. Although homogenization may be accomplished in one stage, it is carried out in two stages for best results. Preferably, the pressure during the first stage is maintained at a minimum of about 2,000 psi and a maximum of about 10,000 psi, most preferably about 3,000 psi, and the pressure during the second stage is maintained at about 500 to 1,000 psi, preferably about 500 psi. The mix is usually maintained at a temperature of about from 60° to 75° C. during homogenization. The emulsion is cooled to a temperature of about from 0° to 25° C. and passed through a whipper for the incorporation of air or an inert gas such as nitrogen, carbon dioxide, nitrous oxide or the like. The whipper may be of conventional construction such as a Hobart mixer or an Oakes continuous mixer that permits cooling of the emulsion to temperatures of about 5° to 15° C., preferably 10° C., during whipping. The emulsion can be whipped to an overrun of from about 100% to 500%, packaged and frozen.

Sugar is employed as the principal source of water soluble solids and typically may range in weight percentage of the composition anywhere from 30% to 60% depending upon the particular sugar and sugar mixture relied upon to offer the desired bacteriostatic protection. Lower amounts of sugar may be used if offset by increased levels of other solutes. As the moisture content of the product increases in the intermediate-moisture range, the level of a given sugar will generally correspondingly increase in order to maintain a sufficient bacteriostatic effect. The level of sugar chosen will also vary depending upon the pressure and level of auxiliary water soluble solids also offering a similar increase in osmotic pressure to the aqueous phase of the composition; thus, a variety of low average molecular weight materials may be included as part of the water soluble solids in the aqueous phase and will augment the sugars in their role of providing sufficient osmotic pressure to prevent bacterial decomposition.

The term "water soluble solids" is used to apply to any additive material which is substantially soluble in water at room temperature or at temperatures comparable to those practices in processing the ingredients of the foods. Included in the class of water soluble non-sugar solids that can be employed are certain inorganic salts used at a level compatible with palatability requirements, e.g., sodium chloride and potassium chloride. Indeed, certain compounds like the diols and polyols, propylene glycol, sorbitol, glycerol and the like which have another function, i.e., as an antimycotic and/or texturizer, may also be relied upon to provide the soluble solids (or solutes) employed in the aqueous phase for bacteriostatic protection. Propylene glycol is prominent in this respect since it is capable of serving a multiple role as mold inhibitor, plasticizing humectant for texture, and component of the water soluble solids of the aqueous phase. The higher diols, such as the aliphatic 1,3-diols containing four to fifteen carbon atoms in the aliphatic chain and their esters which are completely metabolized, can also be used, particularly in conjunction with the foregoing sugars and sugar substitutes. These diols also assist in maintaining the foods in a bacteria-, yeast- and mold-free state while providing softness or plasticity to the formulations. These materials are stable, non-volatile oils with good storage and shelf life and appreciable water solubility, and can be readily emulsified and formulated into various food preparations.

The relative weight percent of said water soluble solids to the moisture content of the total product, when initially incorporated into the product during its manufacture and preparatory to packaging, determines the ulimate functionality of the solids in providing the requisite bacteriostatic effect. The level of water soluble solids may be varied as may the level of moisture initially incorporated within the aforesaid respective ranges. However, in varying these levels the relationship of water soluble solids in solution to the water should be controlled so as to afford the desired osmotic pressure. A good general rule to observe in this connection is to be sure that the weight of water soluble solids available for solution is at least equal to the weight of the moisture present, although in some cases it is possible that a lower level of water soluble solids might afford some protection against microbiological decomposition provided an equivalent degree of osmotic pressure is available. Generally, it will be found that the level of sugar that should be employed under the conditions of the present invention will constitute a major percent by weight of the water soluble solids.

Intermediate-moisture foods have a high sugar content which tends to promote nonenzymatic browning. This phenomenon is caused by complex reactions between the amino groups of proteins and the keto groups of sugars and is known as the Maillard Reaction. This nonenzymatic browning leads to undesirable darkening of the food product as well as off-odors and flavors. These reactions can also reduce the nutritional value of foods. Sugars such as dextrose are known to be capable of use at a lower level than sucrose to achieve an equivalent bacteriostatic effect but are reducing saccharides which are prone to undergo the undesirable Millard-type reaction. Fructose is even more susceptible to the browning reaction. This reaction and other oxidative reactions are progressively retarded as the temperature is lowered from room temperature to refrigerator temperature to freezer temperature. Hence the products of this invention preferably are designed for usage at refrigerator and freezer temperature unlike the conventional intermediate-moisture foods which are stored and used at room temperature, and thus the foods of this invention can tolerate the large amounts of dextrose and furctose used.

The term "sugar" as it is employed in the present context is to be understood as meaning any of a number of useful saccharide materials which are capable of increasing the osmotic pressure of the water in which they are dissolved, thereby giving rise to the requisite bacteriostatic effect. included in the list of useful sugars are the monosaccharides, disaccharides and polysaccharides and their degradation products; e.g., pentoses, including aldopentoses, methylpentoses, and ketopentoses, like xylose and arabinose; a deoxyaldose like rhamnose; hexoses and reducing saccharides such as aldohexoses like glucose, galactose and mannose; the ketohexoses, like fructose and sorbose; disaccharides, like lactose and maltose; non-reducing disaccharides such as a sucrose and other polysaccharides such as dextrin and raffinose; and hydrolyzed starches which contain as their constituents oligosaccharides. Typically, the commercially available mixtures of invert sugars are used which contain dextrose and levulose, as well as maltose and corn syrup solids. The sugars should be of a low molecular weight so as to offer a substantial effect in increasing the osmotic pressure of the sugar solution. The polyhydric alcohols may be used to replace a portion of the sugars used in this invention and are therefore encompassed by that term, i.e., from about 0.5 to 5% of the formulations may be a polyhydric alcohol such as glycerol and the like.

Since the product of this invention, when prepared in the manner herein disclosed, is characterized by its substantial resistance of bacterial decomposition, but may serve as a host for yeasts and mold, the foods of this invention may have an antimycotic agent incorporated at a level sufficient to prevent the growth of such organisms. Sorbate salts such as potassium sorbate, as well as sorbic acid can be used either separately or in combination. Propylene glycol, which may be used alone or with other humectants like sorbitol to impart a further degree of product softness or tenderness, can also serve as an antimycotic. Other antimycotic agents will be apparent to those skilled in the art. The amount of antimycotic agent added is selected so as to produce the desired results and will constitute only a minor proportion of the product, about 0.1% or higher, depending on the particular antimycotic and the particular product composition, although even lower levels, on the order of 50 p.p.m., can be employed in the case of such antimycotics as pimarcin. Potassium sorbate in a water solution can be sprayed onto the surface of the food or the food can be dipped in this solution; other antimycotics which lend themselves to such surface application are esters of the parabens (parahydroxy benzoate) such as propyl and methyl parabens (methyl para-hydroxy benzoate). Cellophane and other enwrapments for the food can be spray-coated with a sobic acid solution, but impregnation or dusting with sorbic acid or potassium sorbate is preferred. Antimycotics which can generally be used are benzoic acid, sodium benzoate, propionic acid, sodium and calcium propionate, sorbic acid, potassium and calcium sorbate, propylene glycol, diethyl pyrocarbonate, and menadione sodium bisulfite (vitamin K).

Other ingredients known to those skilled in the art may also be employed to impart their characteristic effects to the composition of the present ivention. Typical of such ingredients are flavoring agents, colorants, vitamins, minerals, and the like. Suitable flavoring agents can be employed to impart vanilla, cream, chocolate, coffee, maple, spice, mint, butter, caramel, fruit and other flavors. Further, fruit which may not be infused with solutes, may be added to some products of this invention. In addition, certain polyols, such as sorbitol and mannitol, can be employed to modify mouthfeel. Furthermore, other additives, such as phosphates and the like, may be employed for their known functions. Several types of ingredients which can be employed are described below.

Flats high in unsaturation are safflower oil, corn oil, soybean oil, cottonseed oil and sunflower oil. Unsaturated fats as used in this specification are those having an iodine value of about at least 50 which include partially hydrogenated fats and the more highly unsaturated fats with an iodine value above about 100. These fats are recommended for dietary purposes, particularly for those people with a high plasma cholesterol level, a condition associated with atherosclerosis.

The saturated fats include the hydrogenated oil products of coconut, cottonseed, corn, soybean, peanut, olive, etc. Fats having a melting point of 90°-94° F. are preferred, i.e., the melting point should be below body temperature.

Emulsifiers are necessary ingredients of those compositions of the present invention which contain fats and are oil-in-water emulsions. A wide variety of emulsifiers may be employed in amounts on the same order as in the prior art oil-in-water emulsions, for example, about from 0.1-5%, and preferably about from 0.2-1.5%. They induce the formation of a stable emulsion and improve the rate of aeration and the total aeration obtained. Among the more suitable emulsifiers are: hydroxylated lecithin; mono-, di- or polyglycerides of fatty acids, such as monostearin and monopalmitin; polyoxyethylene ether of fatty esters of polyhydric alcohols, such as the polyoxyethylene ethers of sorbitan monostearate (polysorbate 60) or the polyoxyethylene ethers of sorbitan distearate; fatty esters of polyhydric alcholos such as sorbitan monostearate; mono- and diesters of glycols such as propylene glycol monostearate, propylene glycol monopalmitate, and succinoxylated monoglycerides; and the esters of carboxylic acids such as lactic, citric, and tartaic acid with the mono- and diglycerides of fatty acids such as glycerol lacto palmitate and glycerol lacto stearate. The fatty acids employed in the preparation of the emulsifiers include thsoe derived from beef, tallow, and coconut, cotton seed, palm, peanut, soybean and marine oils. Many blends of emulsifiers are commerically used and readily available in accordance with techniques. For example, it may be desirable to provide a controlled hydrophil-lipophil balance (HLB) as with a lipophilic emulsifier such as glyceryl monostearate of sorbitan monostearate with a hydrophilic material such as polysorbate 60.

The emulsion compositions of the present invention also include one or more stabilizers or hydrophilic colloids to imporove the body and texture of toppings, and as an aid in providing freeze-thaw stability. These stabilizers are natural, i.e., begetable, or synthetic gums and may be, for example, carrageenin, guar gum, alginate, xanthan gum and the like, or methylcellulose (Methocle 65 HG), micro-crystalline cellulose and the like, or mixtures thereof. Typically, a gum or combination of gums is employed with a sugar, e.g., dextrose carrier. The amount of these stabilizers can be varied widely in accordance with the amounts required in prior art compositions, generally about from 0-2%, and preferably about from 0.1-0.5%.

Starches useful in this invention include the new and chemically modified starches from potato, arrow root, corn, rice, wheat, waxy maize, sorghym and waxy sorghum. Tapioca starch is particularly suitable for puddings. Generally about from 0.5 to 2.5% starch is adequate, although in the absence of stabilizers or in some puddings up to about 7% may be used.

Protein concentrates and isolates are useful in improving the nutritional qualities of the product and in facilitating and maintaining a whipped structure. Protein also aids in emulsification and contributes to flavor. Bland protein concentrates with a wide range of fiber content, bland soy flour, milk powder and food proteins are all useful, generally in concentrations about from 0-10%, and preferably about from 0.3-3%. Alternatively, use can be made of a protein such as sodium or calcium caseinate, which is conventional in whipped toppings, or as its substitute, a protein hydrolysate in a minor amount.

Many types of salts are used in the compositions of this invention for flavoring, including common salt (sodium chloride), sodium or potassium phosphates, citrates, chlorides, and the like, in amounts about from 0-5%, but preferably about from 0.1-1%.

Antioxidants such as butylated hydroxytoluene, butylated hydroxyanisole and tertiary butyl hydroquinone may be used in minor amounts (i.e., Texon 22 antioxidant).

food grade acidulants such as phosphoric, tartaric, malic, citric, fumaric, hydrochloric and the like edible food acids are suitable to impart tartness, control pH or serve as preservatives.

The following are among the ingredients used in this invention:

The fructose-dextrose syrup used in this invention ("Iso-sweet") comprises 29% water and 71% sugar (50% dextrose, 42% fructose, 1.5% maltose, 1.5% isomaltose and 5% higher saccharides). A high fructose-dextrose syrup contains 23.5% water, with the remaining proportion consisting of 55% fructose and 45% dextrose. A fructose concentrate is an aqueous syrup having 80% sugar, of which 90% is fructose and the remainder is dextrose.

Soy protein concentrate is prepared from soybean flakes which are extracted with a solvent system wherein the major protein fraction is immoblized and the water-soluble carbohydrates, mineral matter, and other minor constituents are removed. The extracted product is dried and ground. The concentrate is sold under the name Promsoy-100 by Central Soya. Whey protein concentrate is sold under the name Empro-50, and contains 53.6 parts protein and 26.5 parts lactose. A delactosed whey protein may also be used.

soybeam oil type 106 is a 100% soybeam oil lightly hydrogenated to an iodine value of 106.

Hard butter type 106 is a blend of 45% palm kernel oil rearranged with 5% palm oil and 50% kernel oil hydrogenated to a Wiley Melting point of 106° F., and having an maximum iodine value of 1.5.

A standard mixture of mono-and diglycerides is used in many formaulations. It is sold under the name Drewmulse 20 by PVO International, Inc., Boonton, New Jersey, and contains about 43% alpha mono content. It has an iodine value of 2.5, a melting point of 140° F. and is manufactured by the glycerolysis of animal or vegetable based fats.

Tenderex emulsifier is a mixture containing polysorbate 60 (11.9%), sorbitan monostearate (31.6%), mono- and diglycerides or fatty aicds (2.3%), propylene glycol (9.5%) and water (44.3%).

The foregoing conventional ingredients may be used in their normal amounts and may vary from the representative amounts and ranges given herein. Food formulations and ranges of ingredients do not readily permit of fixed parameters becuase of variations in people and places. The folllowing examples are not intended to be limiting, but rather illustative of some approaches taken and of course which may be varied in accordance with the spirit and scope of this description.

Further examples appear in the applicants' copending application Ser. No. 763,613, filed Jan. 28, 1977 now U.S. Pat. No. 4,146,652.

EXAMPLE

A product having wide commerical application is sugared egg yolks. Such product is used in commercial bakeries, and by manufacturers of baby foods. The sugared yolk product, which is subject to government regulation, contains egg yolks, sugar, water and up to about 1% of additives such as stabilizers. However, upon freezing, present sugared yolk products become rock-hard, and must be thawed before such products can be employed in the preparation of other food products, e.g., the sugar yolk product is too hard for immediate introduction into blenders and mixers. The period needed to permit thawing of present sugared yolk products, in addition to being an annoyance, provides an opportunity for contamination of the sugared yolks and for microbial growth.

In accordance with the present invention a sugared yolk product was made which will remain non-crystalline at freezer temperature. This product, accordingly, will be immediately available for use by the food industry in that it can be introduced into mixers and blenders without a thawing period. Furthermore, within about 5 to 10 minutes from introduction of this product to room temperature, it will be spoonable.

The sugared yolk formulation comprises about 45 to 85% egg yolks, and preferably about 55 to 70% egg yolks, about 10 to 30% sugar, about 5 to 10% water and up to about 1% of a protein stabilizer. The sugar used is substantially, 75% or more, dextrose plus fructose. The water activity of the sugared yolk product of this invention will be from about 0.85-0.90, up to about 0.93.

a sugared yolk formulation was made from the following ingredients in the indicated amounts.

| Ingredients | Amount |
| --- | --- |
| (1) Dextrose | 8.38 |
| (2) Fructose-Dextrose Syrup | 30.26 |
| (3) Egg Yolk | 60.52 |
| (4) Stabilizer | 0.84 |

Egg Yolks are about 55% water, about 25 to 30% fat, about 15% protein, and miscellaneous minerals, vitamins and other substances. The above formulation contains about 40% water and about 32% fructose plus dextrose.

Ingredients (1) through (4) are mixed at low speed for about 2 to 3 minutes. After a homogenous blend is obtained, the mixture is whipped at high speed for about 3 to 5 minutes.

The formulation is non-crystalline at freezer temperatures. After about 5 to 10 minutes at room temperature, the formulation is spoonable.

The effect of quinine salt addition to the food products of this invention is a reduction in the sweetness of the food product as perceived upon ingestion of the foodstuff. In many cases, the decreased perception of sweetness associated with the quinine-imbued food product is on the order of 50% of that of the unmodified composition. Addition of quinine substances to food products to lessen the perceived sweetness of such compounds is postulated to be achieved through masking of the excessive sweetness occasioned by the sugar through the inherent bitterness of the quinine substance. It is further believed that this bitterness reduces the duration of perceived sweetness by altering the manner in which the sweetness of the sugar is physiologically perceived. This theory of offered solely by means of explanation, however and is not intended to limit the scope of the above invention exclusively to this theory.

This invention has been described in terms of specific embodiments set forth in detail, but it should be understood that these are by way of illustration only and that the invention is not necessarily limited thereto. Modifications and variations will be apparent from this disclosure and may be resorted to without departing from the spirit of this invention, as those skilled in the art will readily understand. Accordingly, such variations and modifications of the disclosed products are considered to be within the scope of this invention and the following claims.

What is claimed is:

1. A microbiologically stable sugared egg yolk food product comprising egg yolk, water, sugar, and flavoring, wherein the product is substantially non-crystalline at freezer temperatures and comprises from about 15 to 55% water, sugar in a ratio to water of about from 0.8-2:1 and a minor but effective amount of flavoring, wherein the solutes content is adequate to provide the product with a water activity of about 0.8-0.9, the amount of fat is less than the amount of water, and said sugar component comprising at least about 50% dextrose plus fructose based upon the total sugar content, wherein the foregoing ingredients are effective to provide an egg yolk product which after storage at freezer temperatures is spoonable after a thawing period at room temperature of about 5 to 10 minutes.

2. The product of claim 1 further comprising up to about 125 p.p.m. of a quinine salt selected from the group consisting of quinine sulfate, quinine bisulfate and quinine hydrochloride.

3. The product of claim 1 further comprising from about 2 at about 75 p.p.m. of a quinine salt selected from the group consisting of quinine sulfate, quinine bisulfate and quinine hydrochloride.

4. A microbiologically stable sugared egg yolk product comprising about 45 to 85% egg yolks, about 10 to 30% sugar, about 5 to 10% water and a small, but effective amount, but not more than 1%, of stabilizer, wherein the amount of dextrose plus fructose is about from 75 to 100% based on the total sugar content, provided that the solutes content is adequate to provide the product with a water activity of about from 0.9, and the foregoing ingredients are effective to provide a product which is non-crystalline at about 10° F.

5. The product of claim 4 comprising between about 55 to 70% egg yolks.

6. The product of claim 4 wherein the amount of fructose is between about 30 to 40% based upon the total sugar content.

7. The product of claim 4 wherein the amount of dextrose is between about 60 to 70% based upon the total sugar content.

8. A method of making a microbiologically stable sugared egg yolk food product which is substantially non-crystalline at freezer temperatures which comprises the steps of:

(a) forming a mixture comprising egg yolk, water, a sugar component, and flavoring, wherein the mixture comprises about from 15 to 55% water, sugar in a ratio to water of about from 0.8 to 2:1 and a minor but effective amount of flavoring, wherein the solutes content is adequate to provide the product with a water activity of about from 0.8 to 0.9, the amount of fat is less than the amount of water, and said sugar component is at least about 50% dextrose plus fructose based upon the total sugar content;

(b) pasteurizing the mixture; and
(c) homogenizing the pasteurized mixture; and
(d) cooling the resultant product to between about -5° F. and 10° F., wherein in the mixture of step (a) the amount of fructose and dextrose in said sugar component and the ratio of sugar component to water are effective to provide an egg yolk product which when stored at freezer temperatures is spoonable after a thawing period of about 5 to 10 minutes at room temperature.

9. The method of claim 8 wherein the mixture formed comprises up to about 125 p.p.m. of a quinine salt selected from the group consisting of quinine sulfate, quinine bisulfate and quinine hydrochloride.

10. A microbiologically stable sugared egg yolk food product comprising egg yolk water, a sugar component and flavoring which is characterized by a water activity of about 0.80 to 0.90, up to about 0.93, and by being substantially non-crystalline at freezer temperatures, wherein said sugar component is at least about 50% dextrose plus fructose based upon the total sugar content, and wherein the amount of fructose plus dextrose, and the ratio of said sugar component to water are effective to provide an egg yolk product which after storage at freezer temperatures is spoonable after a thawing period of about 5 to 10 minutes at room temperature.

11. A method for making a microbiologically stable sugared egg yolk food product which is substantially non-crystalline at freezer temperatures, which comprises the steps of:

(a) forming a mixture comprising about 45 to 85% egg yolks, about 10 to 30% sugar, about 5 to 10% water and an effective amount of a stabilizer, wherein said sugar component is about 75 to 100% of fructose plus dextrose based on the total sugar content, the solutes content is adequate to provide the product with a water activity of from about 0.80 to 0.90, and (b) homogenizing the mixture, and (c) cooling the resultant product to freezer temperatures of from about −5° F. to 10° F., wherein the amount of fructose plus dextrose and the ratio of said sugar component to water in the mixture of step (a) are effective to provide a sugared egg yolk product which after storage at freezer temperatures is spoonable after a thawing period of about 5 to 10 minutes at room temperature.

12. The method according to claims 8 or 11 wherein said sugar component includes fructose and dextrose.

13. The method according to claim 12 wherein said mixture of step (a) is comprised of about 40% water and about 32% fructose plus dextrose.

14. The product according to claims 1, 4 or 10 wherein said sugar is comprised of about 90% fructose and about 10% dextrose.

15. The product according to claims 1, 4 or 10 wherein said sugar is comprised of about 50% dextrose and about 42% fructose, the remainder of said sugar component being comprised of maltose, isomaltose and higher saccharides.

16. A microbiologically stable sugared egg yolk food product comprising about 45 to 85% egg yolk, about 5 to 10% water, about 10 to 30% of a sugar component, flavoring, and a stabilizer, which is characterized by a water activity of about 0.8 to 0.90, up to about 0.93, wherein said sugar component is at least about 75 to 100% fructose plus dextrose based upon the total sugar content, wherein the foregoing ingredients are effective to provide a sugared egg yolk product which is substantially non-crystalline at about 10° F.

* * * * *